United States Patent [19]

Hagen

[11] Patent Number: 5,133,711
[45] Date of Patent: Jul. 28, 1992

[54] ELECTRIC SURGICAL HIGH-FREQUENCY INSTRUMENT

[75] Inventor: Alfred Hagen, Tuttlingen, Fed. Rep. of Germany

[73] Assignee: Delma elektro- und medizinische Apparatebau Gesellschaft mbH, Tuttlingen, Fed. Rep. of Germany

[21] Appl. No.: 498,305

[22] Filed: Mar. 23, 1990

[30] Foreign Application Priority Data

Apr. 7, 1989 [DE] Fed. Rep. of Germany ....... 3911416

[51] Int. Cl.$^5$ .............................................. A61B 17/39
[52] U.S. Cl. ........................................ 606/38; 606/39; 606/40
[58] Field of Search ............................. 606/37, 40, 35

[56] References Cited

U.S. PATENT DOCUMENTS

| | | | |
|---|---|---|---|
| 4,114,623 | 9/1978 | Meinke et al. | 606/39 |
| 4,271,837 | 6/1981 | Schuler | 606/39 |
| 4,860,745 | 8/1989 | Farin et al. | 606/40 |
| 4,969,885 | 11/1990 | Farin | 606/38 |

FOREIGN PATENT DOCUMENTS 3608833  9/1987  Fed. Rep. of Germany ........ 606/40

Primary Examiner—Lee S. Cohen
Attorney, Agent, or Firm—Townsend and Townsend

[57] ABSTRACT

This invention relates to an electric surgical HF instrument having an HF source (12) to which an inactive electrode (18) for tissue contact (17) and an active electrode (16) for surgical treatment can be connected via electrical conductors (15, 15'). The conductor of the active electrode (16) features an antifaradization capacitor (13). A control circuit (20, 21, 22, 23) for sensing a direct current component in the HF circuit is connected to at least one of the electrodes and furnishes an output signal for controlling the HF source (12). The control circuit features a proportional discharge detector circuit (20), the input end of which is connected via connecting leads (19, 19') and conductors (15, 15') to the electrodes (16, 18). The output of the discharge detector circuit (20) is connected to one input of a threshhold switch (22) which controls the HF source (12).

13 Claims, 2 Drawing Sheets

ELECTRIC SURGICAL HIGH-FREQUENCY INSTRUMENT

BACKGROUND OF THE INVENTION

1. Field of the Invention

The present invention relates to an electric surgical high-frequency instrument having an HF (high frequency) source to which an inactive electrode for tissue contact and an active electrode for surgical treatment can be connected via electrical conductors. More particularly, the present invention relates to such an instrument which includes an antifaradization capacitor in the electrical conductor of the active electrode and which also includes a control circuit for sensing a direct current component in the HF circuit which is connected to at least one of the electrodes and which furnishes an output signal for controlling the HF source.

2. Brief Description of the Relevant Art

One such known electric surgical high-frequency instrument (DE-PS 28 01 833) is connected to a variable souce of HF current with an inactive electrode for tissue contact and an active electrode for tissue cutting via an antifaradization capacitor. The binding posts of the antifaradization capacitor are connected to corresponding inputs of an amplifier furnishing a voltage signal to an input of a differential circuit, the other input receiving a reference voltage. The differential voltage generates a control signal for the source of HF current depending on the applied voltages.

Tests on such an instrument have shown that the voltage sensed at the antifaradization capacitor is not suitable to generate a signal for satisfactory control of the HF source and thus for control of the electric arc necessary for cutting.

SUMMARY OF THE INVENTION

The object of the present invention is to create an electric surgical high-frequency instrument of the kind aforementioned, the output power of which is automatically controlled to achieve an electric arc which is suitable at all times for tissue cutting.

This object is achieved by the invention featuring a proportional discharge detector circuit in the control circuit, the input end of which is connected to the electrodes whilst its output is connected to one input of of a comparator circuit controlling the source of HF current.

By connecting a proportional discharge detector circuit—the output of which is connected to one input of a comparator circuit controlling the HF source—to the electrodes, i.e., to the active electrode provided for the surgical treatment and to the inactive electrode, the invention detects any DC voltage resulting in the HF circuit due to unbalanced discharge phenomena and enables this DC voltage to be used to control the HF source.

In a first practical embodiment of the invention the discharge detector circuit comprises a current-compensated choke acting as the source of DC voltage, thus causing the discharge detector circuit—the output end of which corresponds practically to a source of DC voltage—to form an excellent block against high-frequency oscillations, since the impedance of a current-compensated choke is fully effective when the oscillations are unbalanced. The discharge detector circuit thus furnishes a very smooth DC voltage which changes in proportion to the strength of the electric arc struck between the tissue and the active electrode and is not superimposed upon by oscillations of any other kind.

Accordingly, the voltage sensed at the output end of the discharge detector circuit can be satisfactorily used for control of the source of HF current.

In another embodiment of the invention the comparator circuit is an adjustable threshold switch, this adjustable threshold switch being connected via a variable resistor.

This embodiment enables the threshold switch to be used both for coarse adjustment and for fine control of the electric arc struck between the active electrode and the tissue. The coarse adjustment, which is preferably achieved by simple means involving a variable resistor, is performed depending on the desired application of the electrical surgical high-frequency instrument. Criteria for this adjustment may include, the desired degree of sharpness in cutting, whether the application is for contact coagulation, for fulguration, etc. On the basis of the mean power level selected by the coarse adjustment, fine control of the HF source is then performed as a function of the voltage available at the output of the proportional discharge detector circuit.

In one preferred embodiment of the invention the comparator circuit features a microprocessor for receiving the set-point value of the output signal of the discharge detector circuit. By using a microprocessor according to the invention as the comparator circuit the various control variants can be performed for the HF source without necessitating any substantial changes to the configuration of the HF instrument.

In a further embodiment of the invention the microprocessor can receive a value for reducing the setpoint value and the microprocessor is supplied a signal indicating tuning of the control circuit to cause the setpoint value for the output signal of the discharge detector circuit to be switched from the applied setpoint value to a reduced setpoint value as soon as the control circuit is tuned for the first time.

Monitoring tuning of the control circuit in this way according to the invention enables the HF source to be controlled as a function of the input setpoint firstly during tuning and then subsequently as a function of the reduced setpoint, thus ensuring not only an optimum glow discharge between the active electrode and the tissue but also an optimum start of cutting to particular advantage.

To improve the safety of the HF instrument according to the invention a circuit is provided to produce DC decoupling of the discharge detector circuit from the comparator circuit.

In one practical embodiment of the invention this decoupling circuit is designed to provide DC decoupling to a voltage of at least 4 kV, the decoupling circuit featuring an optocoupler followed by an amplifier.

A further improvement of the invention is achieved by including a second antifaradization capacitor in the conductor of the inactive electrode. The first advantage achieved by this second capacitor is that the DC components in the high-frequency circuit are detected even more precisely by the discharge detector circuit, thus providing extremely precise control of the HF source or electric arc. The second advantage provided at the same time by the second antifaradization capacitor is that even if there is a defect in the insulation of the HF course of patient cannot come into direct contact with the operating voltage of the HF instrument as applied to the HF source when being treated with the HF instrument according to the invention.

Yet a further embodiment of the invention features an HF drain current limiter circuit between the antifaradization capacitors and the active and inactive electrodes in the conductors, this HF drain current limiter circuit having a choke of high coupling capacity.

This arrangement permits eliminating, in particular, the negative effects of a change in the capacitive response, since changes in the capacity caused by the line capacities of the electrodes to be connected, can practically be ignored due to the high coupling capacity of the HF drain current limiter circuit provided according to the invention.

In addition, the HF drain current limiter circuit provided according to the invention acts as a filter to block oscillations having a higher frequency than the operating frequency of the HF source.

Use of the RF drain limiter circuit is particularly advantageous when the coupling capacity of the choke amounts to 200 pF thru 400 pF, preferably 250 pF thru 350 pF, but in particular 300 pF.

Other advantages and features of the invention will become apparent in view of the drawings and following detailed description.

DETAILED DESCRIPTION OF THE PREFERRED EMBODIMENTS

Figure 1:
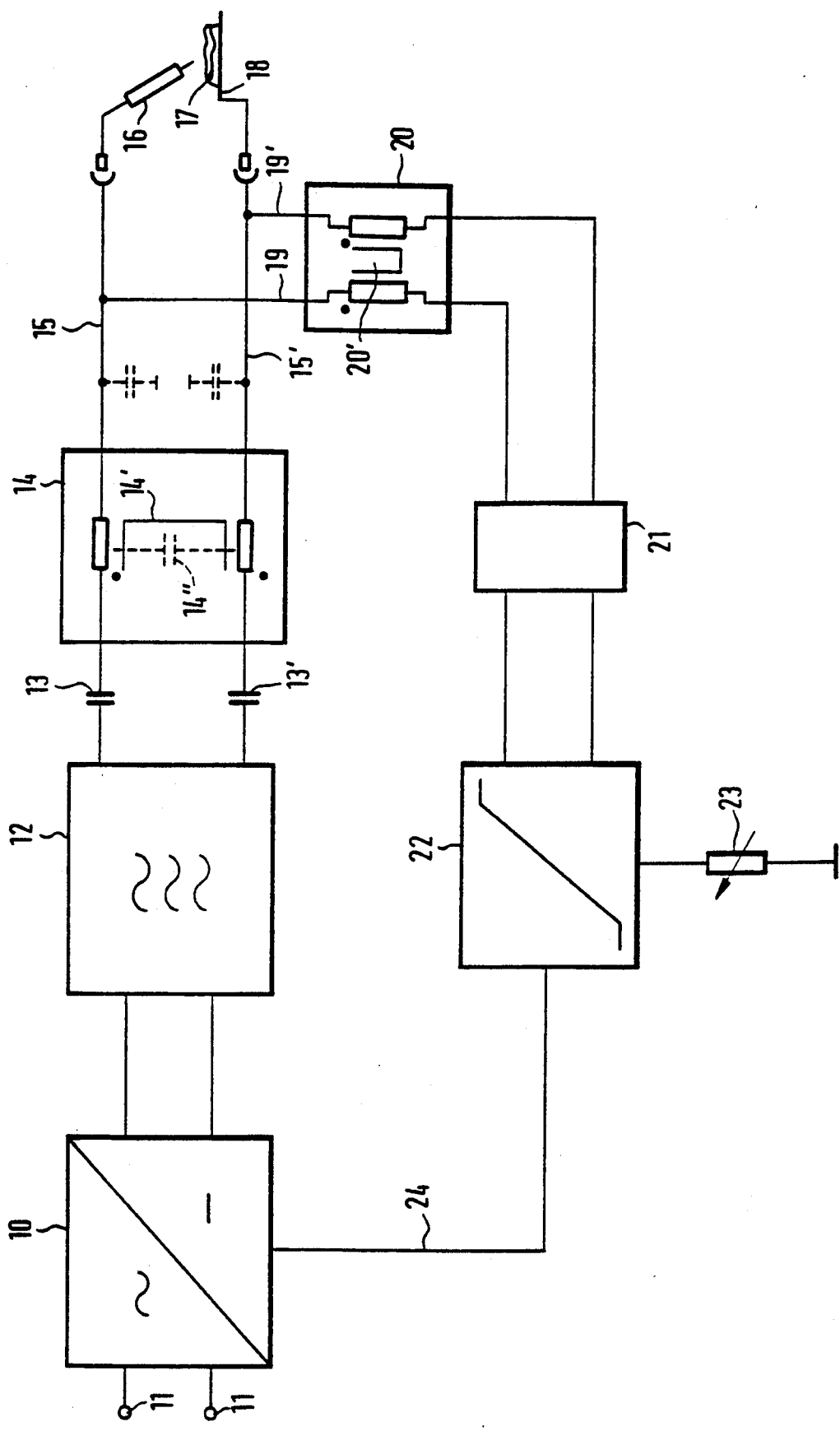
FIG. 1 shows a schematic block diagram of an electric surgical HF instrument and FIG. 2 shows a schematic block diagram of a further electric surgical HF instrument.

Circuit components corresponding to each other are identified by the same reference numerals in both figures of the drawings.

FIG. 1 shows the electric surgical HF instrument as having a power supply 10 with a control circuit, not shown in more detail, the AC voltage end of which can be connected via binding posts 11 to an electrical mains supply and the DC voltage end of which is connected to an HF (high frequency) source 12. The HF source 12 is connected via a first and a second antifaradization capacitor 13, 13' to an HF drain current limiter circuit 14 to which an active electrode 16 for cutting or coagulating tissue 17 can be connected via a first conductor 15. By mans of a second conductor 15' an inactive electrode 18 can be connected to the HF drain current limiter circuit 14 which can be brought into large-surface contact with the tissue 17.

Via connecting leads 19 and 19', respectively, the conductors 15, 15' connect a proportional discharge detector circuit 20 comprising a current-compensating chock 20' acting as a source of direct current. The outputs of the discharge detector circuit are connected to a decoupling circuit 21 which incorporates, for instance, an optocoupler followed by an amplifier, to provide DC decoupling to a minimum of 4 kV, as far as voltage is concerned, between the mains and a patient being treated. The output end of the decoupling circuit 21 is connected to a threshold switch 22 which can be adjusted by means of a variable resistor 23 connected to ground (GND). The output signal of the variable threshold switch 22 is connected via a control lead 24 to the power supply 10 to control the controlling device of the power supply.

The HF drain current limiter circuit 14 comprises a choke 14' of high coupling capacity, i.e. of the order of 300 pF, and which is indicated in the drawing by the capacitor 14" shown dotted.

The function of the described electric surgical HF instrument will now be explained in the following:

For cutting the tissue 17 which is in contact with the inactive electrode 18 by means of the active electrode 16 the HF source 12 generating a high-frequency AC voltage of approx. 500 kHz furnishes the HF power necessary for forming an electric arc between the active electrode 16 and the tissue 17 via the antifaradization capacitors 13, 13', the HF drain current limiter circuit and the conductors 15,15' to the electrodes 16,18.

The antifaradization capacitor 13 in a conductor of the active electrode 16 has maximum capacity of 5 nF and may be manadatory to prevent faradic effects. To enhance the safety of the electric surgical HF instrument and to simultaneously improve suppression of faradic effects, a second antifaradization capacitor 13', may be provided in the conductor of the indifferent electrode 18 which can assume a maximum capacity of 22 nF. By using the two antifaradization capacitors it is ensured that even when there is a defect in the insulation in the HF source 12 the patient cannot come into contact with the operating voltage of the power supply 10.

The choke 14' of the HF drain current limiter circuit 14 prevents by reason of its high coupling capacity 14" any substantial change in the capacitive behavior of the HF instrument due to the connection of the conductors or electrodes 16, 18 since the coupling capacity 14" of the choke 14 is large as compared to the conductor capacity. Accordingly any negative effects due to a change in the capacitive behavior are eliminated when the instrument is used in high-frequency surgery.

In addition, the choke 14' of the HF drain current limiter circuit 14 acts as a filter to block oscillation the frequency of which is higher than the operating frequency of the HF source 12.

When an electric arc—which is required for cutting the tissue 17—is formed at the active electrode an unbalanced discharge cycle takes place for the positive and negative half-wave of the high-frequency AC voltage furnished by the HF source 12, because the electron affinity of electrons leaving the tissue 17 is different than that of electrons leaving the active electrode 16. This produces DC components in the high-frequency circuit which are known as faradic effects, the DC components being a measure of the magnitude of the electric arc between the active electrode 16 and the tissue 17.

The current-compensating choke 20' of the discharge detector circuit 20 acts as an excellent blocking filter for HF oscillations due to its fully effective impedance produced in the presence of unbalanced oscillations stemming from the unbalanced discharge action. At the same time it represents a source of DC voltage, the DC voltage of which is determined by the unbalance of the discharge action between the active electrode 16 and the tissue 17 in contact with the inactive electrode 18. This DC voltage can be measured at the secondary end of the current-compensated choke 20', i.e. at the output end of the discharge detector circuit 20 and used as the input for controlling the power of the HF source 12.

For this purpose the DC voltage available at the output of the discharge detector circuit 20 is applied to the variable threshold switch 22 via the decoupling circuit 21. Depending on its setting, the threshold switch determines by means of its variable resistor 23 the power control of the HF source 12 via the control circuit of the power supply 10 and depending on the magnitude of the electric arc, i.e. depending on the magnitude of the voltage present at the output of the discharge detector circuit 20, it either increases or reduces the output power of the HF source 12.

In this arrangement the threshold switch 22 serves for both coarse and fine adjustment.

Coarse adjustment is achieved by setting the voltage threshold which produces a mean output power level of the HF source 12. As a result of the voltage detected by the discharge detector circuit 20 as presented to the threshold switch 22 by the decoupling circuit 21, the control circuit of the power supply 10 is influenced within a specific range and, thus controlling the magnitude of the electric arc.

The electric surgical HF instrument described here can also be used to advantage for contact coagulation in which direct resistive contact is established between the active electrode 16 and the tissue 17. No sparking is permitted during coagulation, as is generally known. Sparking as well as the electric arc produce an unbalanced discharge during cutting so that a DC voltage sensed at the output of the discharge detector circuit 20 during contact coagulation is an indication that sparking has occurred during coagulation.

The appearance of a DC voltage at the output of the discharge detector circuit 20 can thus be used to shut down the HF source, thus providing simple and reliable of ensuring that the HF source 12 is shut down as soon as sparking starts to occur. When a suitable power characteristic of the HF source 12 is selected this procedure can be used to achieve fully automatic controlled coagulation.

Figure 2:
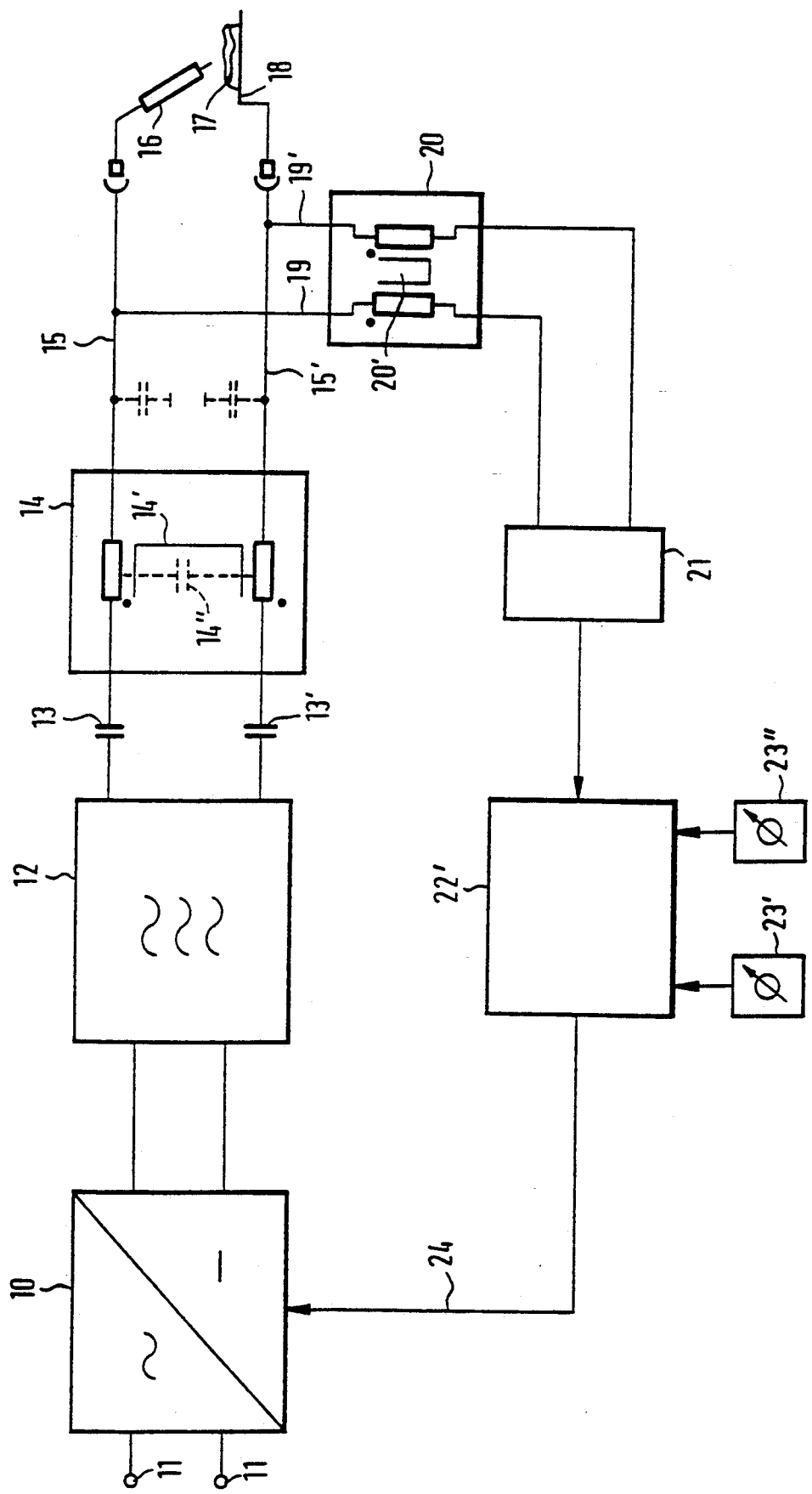

The electric surgical HF instrument shown in FIG. 2 differs from the HF instrument shown in of FIG. 1 merely by a microprocessor 22' taking the place of a threshold switch. Microprocessor: 22'—for receiving the output signal of the decoupling circuit 21—features a first means of adjustment 23' for enabling the input of a setpoint for the output signal of the decoupling circuit 21 and connected to a second means of adjustment 23" with which a value for reducing the setpoint can be entered into the microprocessor 22' as a percentage.

The following describes the function of the electric surgical HF instrument shown in FIG. 2 to the extent that it differs from the HF instrument shown in FIG. 1.

Prior to starting up the HF instrument for cutting the first means of adjustment 23' is used to choose a setpoint for the DC voltage between electrodes 16 and 18 as detected by the discharge detector circuit 20. In addition, a percentage is entered in the microprocessor 22' representing the value of reduction, by means of the second adjustment means 23".

On commencement of cutting the tissue 17 by means of the active electrode 16 the cutting procedure is first monitored and controlled according to the setpoint entered by first adjustment means 23'. At the same time the microprocessor 22' detects tuning of the control circuit. As soon as it detects that the control circuit is tuned for the first time, the microprocessor 22 reduces the entered setpoint according to the value of reduction and performs further control of the cutting procedure as a function of the reduced setpoint. In this way not only is the cutting procedure optimized but also control of the HF instrument is substantially improved during commencement of the cut.

I claim:

1. An electric surgical high-frequency instrument comprising:
   an HF source having first and second outputs and a control input;
   a first antifaradization capacitor, connected by electrical conductor to said first HF source output;
   an active surgical treatment electrode, connected in circuit series by electrical conductor with said first antifaradization capacitor and said first HF source output;
   an inactive tissue contact electrode, connected by electrical conductor to said second HF source output;
   control circuit means for sensing direct current components and for controlling said HF source, said control circuit means comprising:
   circuit means for detecting proportional discharge, having an input end and an output end, said input end connected to at least one of said active and inactive electrodes, said output end producing a proportional discharge signal; and
   circuit means for comparing aid proportional discharge signal and an adjustable threshold signal, connected to said output end of said means for detecting proportional discharge, said circuit means for comparing providing an output signal connected to said control input of said HF source.

2. The electric surgical high-frequency instrument of claim 1, wherein said circuit means for detecting proportional discharge comprises current-compensating choke means for providing a source of DC voltage.

3. The electric surgical high-frequency instrument of claim 1, wherein said circuit means for comparing comprises an adjustable threshold switch.

4. The electric surgical high-frequency instrument of claim 3, wherein said adjustable threshold switch is coupled to ground through a variable resistor.

5. The electric surgical high-frequency instrument of claim 1, wherein said circuit means for comparing comprises microprocessing means for receiving a setpoint value for said output end of said means for detecting proportional discharge.

6. The electric surgical high-frequency instrument of claim 5, wherein said microprocessing means further comprises means for receiving a value for reducing a setpoint value and including means for receiving a signal indicating tuning of said control circuit means to cause switching of the setpoint value for said output end of said means for detecting proportional discharge from the received setpoint value to a reduced setpoint value after said control circuit means has been tuned.

7. The electric surgical high-frequency instrument of claim 1, wherein a second antifaradization capacitor is connected by electrical conductor to said second HF source output and said inactive tissue contact electrode is connected in circuit series by electrical conductor with said second antifaradization capacitor and said second HF source output.

8. An electrical surgical high-frequency instrument comprising:
   an HF source, having first and second outputs and a control input;
   an antifaradization capacitor, connected by electrical conductor to said first HF source output;

an active surgical treatment electrode, connected in circuit series by electrical conductor with said antifaradization capacitor and said first HF source output;

an inactive tissue contact electrode, connected by electrical conductor to said second HF source output;

control circuit means for sensing direct current components and for controlling said HF source, said control circuit means comprising:

means for detecting proportional discharge, having an input end and an output end, said input end connected to at least one of said active and inactive electrodes, said output end producing a proportional discharge signal;

means for providing DC decoupling, having an input and an output, said input of said means for providing DC decoupling being connected to said output end of said means for detecting proportional discharge; and circuit means for comparing said proportional discharge signal and an adjustable threshold signal, connected to said output of said means for providing DC decoupling, said circuit means for comparing providing an output signal connected to said control input of said HF source.

9. The electric surgical high-frequency instrument of claim 8, wherein said means for providing DC decoupling provides voltage-related DC decoupling of at least 4 kilovolts.

10. The electric surgical high-frequency instrument of claim 8, wherein said means for providing DC decoupling further comprises an optocoupler coupled to an amplifier.

11. An electric surgical high-frequency instrument comprising:

an HF source, having first and second outputs and a control input;

an antifaradization capacitor, connected by electrical conductor to said first HF source output;

circuit means for limiting drain current, having first and second inputs and first and second outputs, said first input of said circuit means connected in circuit series by electrical conductor with said antifaradization capacitor and said first HF source output, said second input of said circuit means connected by electrical conductor to said second HF source output;

an active surgical treatment electrode, connected by electrical conductor with said first output of said circuit means for limiting drain current;

an inactive tissue contact electrode, connected by electrical conductor to said second output of said circuit means for limiting drain current;

control circuit means for sensing direct current components and for controlling said HF source, said control circuit means comprising:

means for detecting proportional discharge, having an input end and an output end, said input end connected to at least one of said active and inactive electrodes, said output end producing a proportional discharge signal; and circuit means for comparing said proportional discharge signal and an adjustable threshold signal, connected to said output end of said means for detecting proportional discharge, said circuit means for comparing providing an output signal connected to said control input of said HF source.

12. The electric surgical high-frequency instrument of claim 11, wherein said circuit means for limiting drain current comprises a high-coupling-capacity choke.

13. The electric surgical high-frequency instrument of claim 12, wherein said high-coupling-capacity choke has a coupling capacity in the range of 200 pF to 400 pF.

* * * * *